United States Patent [19]

Holtkamp, Sr.

[11] Patent Number: Plant 7,005

[45] Date of Patent: Aug. 29, 1989

[54] AFRICAN VIOLET PLANT NAMED MARTINIQUE

[76] Inventor: Reinhold Holtkamp, Sr., Werther Strasse 112, D4294 Isselburg, Fed. Rep. of Germany

[21] Appl. No.: 244,030

[22] Filed: Sep. 12, 1988

[51] Int. Cl.[4] ..... A01H 5/00
[52] U.S. Cl. ..... Plt./69
[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and distinct cultivar of African violet named Martinique characterized by its single, blue flowers with slightly frilled white edges; strong, upright flower stems that curve slightly toward the center to form a compact bouquet above the leaves; bright green, oval to heart-shaped, serrated leaves with a bright center; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Martinique.

The new cultivar was referred to during the breeding and selection process by the designation I 6X96/105 and is a product of a planned breeding program. The new cultivar was originated from a cross made by me in the controlled breeding program in Haffen, Federal Republic of Germany. The female, or seed parent was a cultivar designated XVX249. The male, or pollen parent was a cultivar designated E 40/2.

Martinique was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Martinique has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice. The following traits have been repeatedly observed and are determined to be basic characteristics of Martinique, which in combination distinguish this African violet as a new and distinct cultivar:

(1) Strong, upright flower stems curving slightly toward the center.
(2) Single, violet-shaped blue flowers with slightly frilled white edges.
(3) Profuse flowering.
(4) Each plant carries 7 and more upright flower stems each of which carries 7–10 and more flowers.
(5) Long lasting, non-dropping flowers.
(6) Vigorous grower.
(7) Plant saleable 10 to 11 weeks after potting.
(8) Seed capsules push slightly through.

(9) Oval to heart-shaped medium green, serrated leaves.
(10) After maturity the flowers dry off, and remain on the peduncle without becoming infected by botrytis.

The blue flowers with white edges of Martinique ressemble somewhat those of the variety Barbados. However, Martinique and Barbados are different in all other respects.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2 p.m. in Nashville, Tenn.

Botanical classification: *Saintpaulia ionantha,* Ramat., c.v. Martinique.

Parentage:

*Male parent.*—E 40/2.

*Female parent.*—XVX249

Propagation: The new cultivar holds its distinguishing characteristics through successive propagations by leaf cuttings.

Plant: From 9 cm to 11 cm tall when grown in pots, and approximately 21–23 cm in diameter when fully grown.

*Leaves.*—General form: Oval to heart-shaped. Diameter: 55–65 mm. Texture: Velvety. Aspect: Serrated, hairy, slightly shiny. Veins: Upperside: well visible, brighter green than the leaf at the center, underside: very well pronounced, light green, shiny. Color (upperside): Yellow-Green Group 147 between A and B. Color (underside): Greyed Green Group 194 D. Petiole: Strong upright, light green, occasionally purplish touch on the side towards the flowers, hairy.

*Flowers.*—Buds: Ball-shaped, 8–9 mm just before opening, purple with frilled white edge, hairy. Sepals: five (5). Color: Purplish green. Calyx: Shape: Funnel-shaped. Aspect: Spear-shaped, hairy. Peduncle: Character: Strong upright, hairy. Color: Purplish green. Individual flowers: Size: 35–40 mm. Shape: Single violet-shaped with slightly frilled edges. Color (upperside): Violet-Blue Group 93 B. Under cooler temperatures and more intensive lighting, the blue tends to intensify. Color (underside): Violet-Blue Group 93 C. Borne: Each flower stem carries 7–10 and more flowers on strong, upright peduncle that are free standing above the leaves, thereby forming a compact bouquet. Flowering habit: Flowers 10–11 weeks after potting.

Reproductive organs.—Stamens: Two (2). Anthers: 2 composed of 4 anther cells, seed capsule pushes slightly through. Filaments: Yellowish green, 4–5 mm long. Pollen Color: Yellow Group 7. Styles: 7–8 mm long, purple, base of ovary light green and hairy.

*Roots.*—Normally developed, white when young, turning slightly brownish when older.

Disease resistance: Good.

General observations: Martinique is a very attractive, vigorous and compact grower with bright green, oval to heart-shaped, serrated leaves with an even brighter green center. A tight bouquet of flowers free standing above the leaves develops after approximately 10–11 weeks. Each of the 7 and more strong flower stems carries 7–10 and more single blue flowers with slightly frilled white edges. On older flowers the white edge is not very clear-cut. The bright yellow anthers contrast nicely with the blue color which is darker at the center. Occasionally, 1–2 additional small petals may develop. The flowers are long-lasting and non-dropping and the seed capsules push slightly through.

I claim:

1. A new and distinct cultivar of African violet named Martinique, as described and illustrated, and particularly characterized by its single, blue flowers with slightly frilled white edges; strong, upright flower stems that curve slightly toward the center to form a compact bouquet above the leaves; bright green, oval to heart-shaped, serrated leaves with a bright center; profuse flowering, vigorous and compact growth habit, flowering 10–11 weeks after potting, and its long lasting and non-dropping flowers.

* * * * *

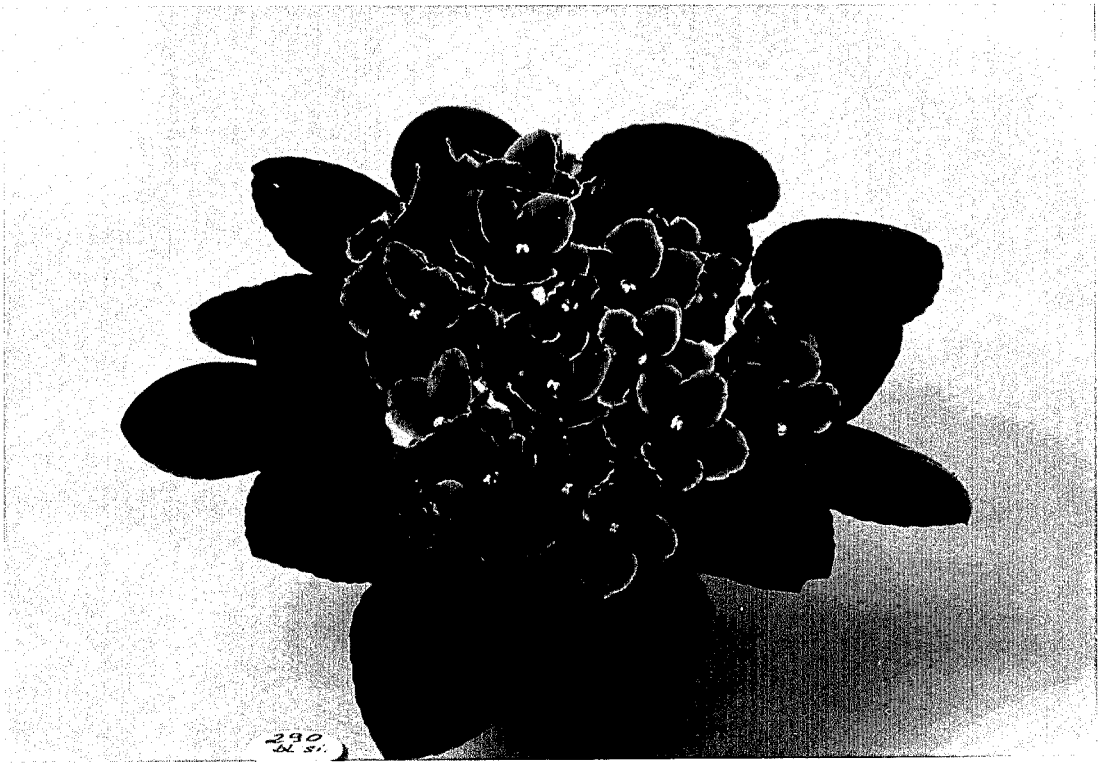
290
DL 51.